United States Patent
Adams et al.

(10) Patent No.: US 6,649,138 B2
(45) Date of Patent: Nov. 18, 2003

(54) SURFACE-MODIFIED SEMICONDUCTIVE AND METALLIC NANOPARTICLES HAVING ENHANCED DISPERSIBILITY IN AQUEOUS MEDIA

(75) Inventors: Edward William Adams, San Francisco, CA (US); Marcel Pierre Bruchez, Jr., Fremont, CA (US)

(73) Assignee: Quantum Dot Corporation, Hayward, CA (US)

( * ) Notice: Subject to any disclaimer, the term of this patent is extended or adjusted under 35 U.S.C. 154(b) by 7 days.

(21) Appl. No.: 09/841,237

(22) Filed: Apr. 23, 2001

(65) Prior Publication Data

US 2002/0045045 A1 Apr. 18, 2002

Related U.S. Application Data

(60) Provisional application No. 60/240,216, filed on Oct. 13, 2000.

(51) Int. Cl.$^7$ .................................................. B32B 5/16
(52) U.S. Cl. ........................................ 423/403; 428/407
(58) Field of Search ................................. 428/403, 407

(56) References Cited

U.S. PATENT DOCUMENTS

| | | | |
|---|---|---|---|
| 4,138,381 A | | 2/1979 | Chang et al. |
| 4,504,618 A | | 3/1985 | Irvine et al. |
| 4,715,986 A | * | 12/1987 | Gruning et al. |
| 5,110,505 A | | 5/1992 | Herron et al. |
| 5,587,446 A | | 12/1996 | Frechet et al. |
| 5,990,479 A | * | 11/1999 | Weiss et al. |
| 6,007,845 A | * | 12/1999 | Domb et al. |
| 6,048,616 A | | 4/2000 | Gallagher et al. |
| 6,150,459 A | | 11/2000 | Mayes et al. |
| 6,162,456 A | | 12/2000 | Dunbar et al. |
| 6,319,426 B1 | * | 11/2001 | Bawendi et al. |
| 6,322,901 B1 | * | 11/2001 | Bawendi et al. |
| 6,326,144 B1 | * | 12/2001 | Bawendi et al. |
| 6,333,110 B1 | * | 12/2001 | Barbera-Guillem |
| 6,342,625 B1 | * | 1/2002 | Kwetkat et al. |
| 6,444,143 B2 | * | 9/2002 | Bawendi et al. |
| 6,468,808 B1 | * | 10/2002 | Nie et al. |

FOREIGN PATENT DOCUMENTS

| | | |
|---|---|---|
| WO | WO 99/50916 | 10/1999 |
| WO | WO 00/17642 | 3/2000 |
| WO | WO 00/17655 | 3/2000 |
| WO | WO 00/17656 | 3/2000 |
| WO | WO 00/29617 | 5/2000 |

OTHER PUBLICATIONS

Antonietti et al. (1997), "Amphiphilic Derivatives of Poly-(Acrylic Acid) as Stabilizer in Emulsion Polymerisation," *Macromol. Rapid Commun.* 18:295–302.
Brust et al. (1995), "Synthesis and Reactions of Functionalised Gold Nanoparticles," *J. Chem. Soc., Chem. Commun.*, pp. 1655–1656.
Carrot et al. (1999), "Synthesis and Characterization of Nanoscopic Entities Based on Poly(Caprolactone)—Grafted Cadmium Sulfide Nanoparticles," *Chem. Mater.* 11(12):3571–3577.
Ekimov et al. (1981), "Quantum Size Effect in Three–Dimensional Microscopic Semiconductor Crystals," *JETP Lett.* 34(6):345–349.
Ingram et al. (1997), "Poly–Hetero–ω–Functionalized Alkanethiolate–Stabilized Gold Cluster Compounds," *J. Am. Chem. Soc.* 119(39):9175–9178.
Johnson et al. (1998), "Influence of a Terminal Functionality on the Physical Properties of Surfactant–Stabilized Gold Nanoparticles," *Langmuir* 14(23):6639–6647.
Kumar et al. (2000), "Phase Transfer of Aqueous CdS Nanoparticles by Coordination with Octadecanethiol Molecules Present in Nonpolar Organic Solvents," *Langmuir* 16(24):9299–9302.
Leff et al. (1996), "Synthesis and Characterization of Hydrophobic, Organically–Soluble Gold Nanocrystals Functionalized with Primary Amines," *Langmiur* 12(20):4723–4730.
Lochhead et al. (1994), "An Investigation of the Mechanism by Which Hydrophobically Modified Hydrophilic Polymers Act as Primary Emulsifiers for Oil–in–Water Emulsions. 1. Poly(Acrylic Acids) and Hydroxyethyl Celluloses," *Colloids and Surfaces A: Physicochemical and Engineering Aspects* 88:27–32.
Ma et al. (1998), "Polymer Micelles from Poly(Acrylic Acid)–*Graft*–Polystyrene," *Macromolecules* 31(6):1773–1778.
Moffitt et al. (1998), "Spherical Assemblies of Semiconductor Nanoparticles in Water–Soluble Block Copolymer Aggregates," *Chem. Mater.* 10(4):1021–1028.
Poncent–Legrand et al. (1999), "Rheological Behaviour of Colloidal Dispersions of Hydrophobic Particles Stabilised in Water by Amphiphilic Polyelectrolytes," *Colloids and Surfaces A: Physicochemical and Engineering Aspects* 152:251–261.
Premachandran et al. (1997), "The Enzymatic Synthesis of Thiol–Containing Polymers to Prepare Polymer–CdS Nanocomposites," *Chem. Mater.* 9(6):1342–1347.

(List continued on next page.)

*Primary Examiner*—H. Thi Le
(74) *Attorney, Agent, or Firm*—Dianne E. Reed; Reed & Eberle, LLP

(57) ABSTRACT

Water-dispersible nanoparticles are prepared by applying a coating of a multiply amphipathic dispersant to the surface of a hydrophobic nanoparticle comprised of a semiconductive or metallic material. The multiply amphipathic dispersant has two or more hydrophobic regions and two or more hydrophilic regions, and is typically polymeric. Preferred polymeric dispersants are comprised of (1) a hydrophobic backbone with hydrophilic branches, (2) a hydrophilic backbone with hydrophobic branches, or (3) a backbone that may be either hydrophobic or hydrophilic, and substituted with both hydrophilic and hydrophobic branches. Monodisperse populations of water-dispersible nanoparticles are also provided, as are conjugates of the water-dispersible nanoparticles with affinity molecules such as peptides, oligonucleotides, and the like.

57 Claims, No Drawings

OTHER PUBLICATIONS

Sastry et al. (1998), "Facile Surface Modification of Colloidal Particles Using Bilayer Surfactant Assemblies: A New Strategy for Electrostatic Complexation in Langmuir–Blodgett Films," *Langmuir* 14(20):5921–5928.

Schaller et al. (1999), "Synthesis and Properties of Hydrophobically Modified Water–Borne Polymers for Pigment Stabilization," *Progress in Organic Coatings* 35:63–67.

Shen et al. (1999), "Bilayer Surfactant Stabilized Magnetic Fluids: Synthesis and Interactions at Interfaces," *Langmuir* 15(2):447–453.

Sidorov et al. (1999), "Stabilization of Metal Nanoparticles in Aqueous Medium by Polyethyleneoxide–Polyethyleneimine Block Copolymers," *Journal of Colloid and Interface Science* 212:197–211.

Spatz et al. (1996), "Gold Nanoparticles in Micellar Poly-(Styrene)–b–Poly(Ethylene Oxide) Films—Size and Interparticle Distance Control in Monoparticulate Films," *Advanced Materials* 8(4):337–340.

Tribet et al. (1997), "Stabilization of Hydrophobic Colloidal Dispersions in Water with Amphiphilic Polymers: Application to Integral Membrane Proteins," *Langmuir* 13(21):5570–5576.

Wang et al. (1999), "Synthesis of Polycarbonate–*co*–Poly-(*p*–Ethylphenol) and CdS Nanocomposites," *Journal of Applied Polymer Science* 72:1851–1868.

* cited by examiner

SURFACE-MODIFIED SEMICONDUCTIVE AND METALLIC NANOPARTICLES HAVING ENHANCED DISPERSIBILITY IN AQUEOUS MEDIA

CROSS-REFERENCE TO RELATED APPLICATIONS

This application claims priority to U.S. Provisional Application No. 60/240,216, filed Oct. 13, 2000.

TECHNICAL FIELD

This invention relates generally to surface-modified nanoparticles, and more particularly relates to surface-modified semiconductor and metal nanoparticles having enhanced dispersibility in aqueous media as well as superior colloidal and photophysical stability. The invention additionally relates to methods for making and using the novel surface-modified nanoparticles. The invention finds utility in a variety of fields, including biology, analytical and combinatorial chemistry, medical diagnostics, and genetic analysis.

BACKGROUND

Semiconductor nanocrystals (also known as quantum dot particles) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) as the size of the nanocrystals gets smaller.

Semiconductor nanocrystals are nanoparticles composed of an inorganic, crystalline semiconductive material and have unique photophysical, photochemical and nonlinear optical properties arising from quantum size effects, and have therefore attracted a great deal of attention for their potential applicability in a variety of contexts, e.g., as detectable labels in biological applications, and as useful materials in the areas of photocatalysis, charge transfer devices, and analytical chemistry. As a result of the increasing interest in semiconductor nanocrystals, there is now a fairly substantial body of literature pertaining to methods for manufacturing such nanocrystals. Broadly, these routes may be classified as involving preparation in glasses (see Ekimov et al. (1981) *JETP Letters* 34:345), aqueous preparation (including preparation that involve use of inverse micelles, zeolites, Langmuir-Blodgett films, and chelating polymers; see Fendler et al. (1984) *J. Chem. Society, Chemical Communications* 90:90, and Henglein et al. (1984) *Ber. Bunsenges. Phys. Chem.* 88:969), and high temperature pyrolysis of organometallic semiconductor precursor materials (Murray et al. (1993) *J. Am. Chem. Soc.* 115:8706; Katari et al. (1994) *J. Phys. Chem.* 98:4109). The two former methods yield particles that have unacceptably low quantum yields for most applications, a high degree of polydispersity, poor colloidal stability, a high degree of internal defects, and poorly passivated surface trap sites. In addition, nanocrystals made by the first route are physically confined to a glass matrix and cannot be further processed after synthesis.

To date, only the high temperature pyrolysis of organometallic reagents has yielded semiconductor nanocrystals that are internally defect free, possess high band edge luminescence and no trapped emission, and exhibit near monodispersity. Additionally, this route gives the synthetic chemist a substantial degree of control over the size of the particles prepared. See Murray et al. (1993), supra. One disadvantage of this method, however, is that the particles are sequestered in reverse micelles of coordinated, hydrophobic surfactant molecules. As such, they are only dispersible in organic solvents such as chloroform, dichloromethane, hexane, toluene and pyridine. This is problematic insofar as many applications that rely on the fluorescence emission of the semiconductor nanocrystals require that the nanocrystals be water soluble or at least water dispersible.

Although some methods for rendering semiconductor nanocrystals water dispersible have been reported, they are still problematic insofar as the treated semiconductor nanocrystals suffer from significant disadvantages that limit their wide applicability. For example, Spanhel et al. (1987) *J. Am. Chem. Soc.* 109:5649, discloses a $Cd(OH)_2$-capped CdS sol; however, the photoluminescent properties of the sol were pH dependent. The sol could be prepared only in a very narrow pH range (pH 8–10) and exhibited a narrow fluorescence band only at a pH of greater than 10. Such pH dependency greatly limits the usefulness of the material; in particular, it is not appropriate for use in biological systems.

Other groups have replaced the organic passivating layer of the semiconductor nanocrystal with water-soluble moieties; however, the resultant derivatized semiconductor nanocrystals are not highly luminescent. Short chain thiols such as 2-mercaptoethanol and 1-thio-glycerol have been used as stabilizers in the preparation of water-soluble CdTe nanocrystals. See, Rogach et al. (1996) *Ber. Bunsenges. Phys. Chem.* 100:1772 and Rajh et al. (1993) *J. Phys. Chem.* 97:11999. Other more exotic capping compounds have been reported with similar results. See Coffer et al. (1992) *Nanotechnology* 3:69, which describes the use of deoxyribonucleic acid (DNA) as a capping compound. In all of these systems, the coated semiconductor nanocrystals were not stable and photoluminescent properties degraded with time.

Thus, to use these high quantum yield materials in applications that require an aqueous medium, one must find a way of changing the polarity of the organic coating, thereby facilitating the transfer of these particles to water. A great deal of work has been conducted on surface exchange reactions that seek to replace the oleophilic hydrocarbon coating on the nanocrystal surface with a range of bifunctional polar molecules wherein one functional group of the capping molecule bears some affinity for the surface of the nanocrystal, while the other functional group, by virtue of its ionizability or high degree of hydration, renders the nanocrystal water soluble. For example, International Patent Publication No. WO 00/17655 to Bawendi et al. describes a method for rendering semiconductor nanocrystals water dispersible wherein monomeric surfactants are used as dispersing agents, with the hydrophobic region of the surfactants promoting association with the nanocrystals, while the hydrophilic region has affinity for an aqueous medium and stabilizes an aqueous suspension of the nanocrystals. International Patent Publication No. WO 00/17656 to Bawendi et al. describes a similar method wherein monomeric compounds of formula $HS-(CH_2)_n-X$, wherein n is preferably $\geq 10$ and X is carboxylate or sulfonate, are used in place of the monomeric surfactants.

Kuno et al. (1997) *J. Chem. Phys.* 106:9869–9882, Mikulec, "Semiconductor Nanocrystal Colloids: Manganese Doped Cadmium Selenide, (Core) Shell Composites for Biological Labeling, and Highly Fluorescent Cadmium Telluride," doctoral dissertation, Massachusetts Institute of Technology (September 1999), and International Patent Publication No. WO 00/17656 to Bawendi et al., cited supra, give detailed descriptions of surface exchange reactions designed to improve the water dispersibility of hydrophobic nanocrystals. In general, these references indicate that: exchange of the original hydrophobic surfactant layer on the nanocrystal surface is never quite complete, with retention of only about 10% to about 15% of the surfactant (even after multiple exchange reactions); although never quantitatively displaced, exchange of the original phosphine/phosphine oxide surfactant layer with more polar ligands results in a substantial decrease in quantum yield that is never entirely regained; once dispersed in water, the particles have limited colloidal stability; and attempts to carry out further chemistry with these particles, such as linking them to biomolecules through their pendant carboxyl functionalities, is highly irreproducible and dependent on the size of the nanocrystal.

Thus, there remains a need in the art for a reliable, reproducible method for rendering hydrophobic semiconductor nanocrystals dispersible in aqueous media while preserving the quantum efficiencies of the original particles, maintaining colloidal stability, and avoiding or minimizing any change in particle size distribution. Ideally, such a method would be useful not only with semiconductor nanoparticles, but also with other types of nanoparticles having hydrophobic surfaces, e.g., semiconductive nanoparticles that are not necessarily crystalline and metallic nanoparticles that may or may not be surface-modified.

SUMMARY OF THE INVENTION

It is accordingly a primary object of the invention to address the aforementioned need in the art by providing surface-modified nanoparticles having enhanced dispersibility in aqueous media, wherein the nanoparticles are comprised of an inner core having a hydrophobic surface and an outer layer of a multiply amphipathic dispersant.

It is still another object of the invention to provide such surface-modified nanoparticles wherein the inner core is composed of a semiconductive or metallic material.

It is yet another object of the invention to provide such nanoparticles wherein the multiply amphipathic dispersant is a polymer having two or more hydrophobic regions and two or more hydrophilic regions.

It is a further object of the invention to provide a method for preparing a population of the aforementioned water-dispersible nanoparticles.

It is still a further object of the invention to provide a composition composed of a nanoparticle conjugate, i.e., a water-dispersible nanoparticle as above, conjugated to an affinity molecule that serves as the first member of a binding pair.

It is yet a further object of the invention to provide such a composition wherein a second member of the binding pair is associated with the first member through either covalent or noncovalent interaction.

It is an additional object of the invention to provide a monodisperse population of water-dispersible nanoparticles wherein the population is characterized in that it exhibits no more than about a 10% rms deviation, preferably no more than about a 5% rms deviation, in the diameter of the inner core.

Additional objects, advantages and novel features of the invention will be set forth in part in the description which follows, and in part will become apparent to those skilled in the art upon examination of the following, or may be learned by practice of the invention.

In one aspect of the invention, then, a water-dispersible nanoparticle is provided that is comprised of an inner core and an outer layer of a multiply amphipathic dispersant, i.e., a compound having two or more hydrophobic regions and two or more hydrophilic regions. The inner core comprises a semiconductive or metallic material, preferably an inorganic semiconductive material that is in a crystalline state. Generally, the inner core also comprises a hydrophobic passivating layer on the semiconductive or metallic material resulting from solvents and/or surfactants used in nanoparticle manufacture. The surface of the inner core is accordingly hydrophobic, and the hydrophobic regions of the dispersant thus have affinity for the core surface and attach thereto, while the hydrophilic regions of the dispersant extend outward from the nanoparticle and provide for dispersibility in water. In a preferred embodiment, the dispersant is polymeric and has a plurality of both hydrophobic regions and hydrophilic regions, thus enhancing water dispersibility of the nanoparticle as well as the dispersant's affinity for the core surface. Particularly preferred dispersants are hyperbranched or dendritic polymers, which, relative to prior methods that involve monomeric dispersants, substantially increase the water dispersibility and colloidal stability of the nanoparticles. In a preferred embodiment, the nanoparticles are luminescent semiconductive nanocrystals, and include an overcoating "shell" layer between the inner core and the multiply amphipathic outer layer to increase luminescence efficiency. The shell material has a higher bandgap energy than the nanocrystal core, and should also have good conduction and valence band offset with respect to the nanocrystal core. Further, an "affinity molecule," i.e., one member of a binding pair, may be attached to the outer layer of the surface-modified molecule, providing a nanoparticle "conjugate" that is useful in detecting the presence or quantity of target molecules that comprise the second member of the binding pair. The affinity molecule may be, for example, a protein, an oligonucleotide, an enzyme inhibitor, a polysaccharide, or a small molecule having a molecular weight of less than about 1500 grams/Mol.

In a related aspect of the invention, then, a composition is provided that is comprised of the aforementioned nanoparticle conjugate in association with the second member of the binding pair, wherein the association may involve either covalent or noncovalent interaction.

In another aspect of the invention, a monodisperse population of surface-modified nanoparticles is provided, comprising a plurality of water-dispersible nanoparticles each having an inner core comprised of a semiconductive or metallic material and, surrounding the inner core, an outer layer comprised of a multiply amphipathic dispersant as described above, wherein the population is characterized in that the nanoparticles are of substantially the same size and shape, i.e., the population exhibits no more than about a 10% rms deviation in the diameter of the inner core, preferably no more than about a 5% rms deviation in the diameter of the inner core. The narrow size distribution of a monodisperse population increases the "information density" that is obtainable as a result of the particles' luminescence, i.e., the number of discrete luminescence emissions obtainable for a given nanoparticle composition.

In another aspect of the invention, a method is provided for making the surface-modified nanoparticles described above. The method involves (a) admixing (i) an amphipathic dispersant comprised of a polymer having two or more hydrophobic regions and two or more hydrophilic regions, with (ii) a plurality of hydrophobic nanoparticles, in (iii) a nonaqueous solvent, to provide an admixture of dispersant and nanoparticles in solution; (b) subjecting the admixture to conditions effective to cause adsorption of the dispersant by the nanoparticles; and (c) transferring the dispersant-coated nanoparticles prepared in step (b) to an aqueous medium such as water or an aqueous buffer.

DETAILED DESCRIPTION OF THE INVENTION

I. Definitions:

Before describing the present invention in detail, it is to be understood that unless otherwise indicated this invention is not limited to specific nanoparticle materials, amphipathic dispersants, or manufacturing processes, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, Aa dispersant≈refers to a single dispersant as well as a mixture of two or more dispersants, "a nanoparticle" encompasses not only a single nanoparticle but also two or more nanoparticles, and the like.

In describing and claiming the present invention, the following terminology will be used in accordance with the definitions set out below.

The term "amphipathic," referring to the dispersants employed herein, is used in its conventional sense to indicate a molecular species having a hydrophobic region and a hydrophilic region. The dispersants herein are "multiply amphipathic" in that they contain two or more hydrophobic regions and two or more hydrophilic regions.

The term "attached," as in, for example, the "attachment" of a dispersant to a nanoparticle surface, includes covalent binding, adsorption, and physical immobilization. The terms "associated with," "binding" and "bound" are identical in meaning to the term "attached."

Attachment of the present multiply amphipathic dispersants to the surface of a metallic or semiconductive nanoparticle will generally involve "adsorption," wherein "adsorption" refers to the noncovalent retention of a molecule by a substrate surface. That is, adsorption occurs as a result of noncovalent interaction between a substrate surface and adsorbing moieties present on the molecule that is adsorbed. Adsorption may occur through hydrogen bonding, van der Waal's forces, polar attraction or electrostatic forces (i.e., through ionic bonding), and in the present case will typically involve the natural affinity of a hydrophobic region of a molecule for a hydrophobic surface.

The term "nanoparticle" refers to a particle, generally a semiconductive or metallic particle, having a diameter in the range of about 1 nm to about 1000 nm, preferably in the range of about 2 nm to about 50 nm, more preferably in the range of about 2 nm to about 20 nm. As discussed elsewhere herein, semiconductive and metallic "nanoparticles" generally include a passivating layer of a water-insoluble organic material that results from the method used to manufacture such nanoparticles. The terms "surface-modified nanoparticle" and "water-dispersible nanoparticle" as used herein refer to the modified nanoparticles of the invention, while the term "nanoparticle," without qualification, refers to the hydrophobic nanoparticle that serves as the inner core of the surface-modified, water-dispersible nanoparticle.

The terms "semiconductor nanoparticle" and "semiconductive nanoparticle" refer to a nanoparticle as defined above that is composed of an inorganic semiconductive material, an alloy or other mixture of inorganic semiconductive materials, an organic semiconductive material, or an inorganic or organic semiconductive core contained within one or more semiconductive overcoat layers.

The term "metallic nanoparticle" refers to a nanoparticle as defined above that is composed of a metallic material, an alloy or other mixture of metallic materials, or a metallic core contained within one or more metallic overcoat layers.

The terms "semiconductor nanocrystal," "quantum dot" and "Qdot™ nanocrystal" are used interchangeably herein to refer to semiconductor nanoparticles composed of an inorganic crystalline material that is luminescent (i.e., they are capable of emitting electromagnetic radiation upon excitation), and include an inner core of one or more first semiconductor materials that is optionally contained within an overcoating or "shell" of a second semiconductor material. A semiconductor nanocrystal core surrounded by a semiconductor shell is referred to as a "core/shell" semiconductor nanocrystal. The surrounding shell material will preferably have a bandgap energy that is larger than the bandgap energy of the core material and may be chosen to have an atomic spacing close to that of the core substrate. Suitable semiconductor materials for the core and/or shell include, but not limited to, the following: materials comprised of a first element selected from Groups 2 and 12 of the Periodic Table of the Elements and a second element selected from Group 16 (e.g., ZnS, ZnSe, ZnTe, CDs, CdSe, CdTe, HgS, HgSe, HgTe, MgS, MgSe, MgTe, CaS, CaSe, CaTe, SrS, SrSe, SrTe, BaS, BaSe, BaTe, and the like); materials comprised of a first element selected from Group 13 of the Periodic Table of the Elements and a second element selected from Group 15 (GaN, GaP, GaAs, GaSb, InN, InP, InAs, InSb, and the like); materials comprised of a Group 14 element (Ge, Si, and the like); materials such as PbS, PbSe and the like; and alloys and mixtures thereof. As used herein, all reference to the Periodic Table of the Elements and groups thereof is to the new IUPAC system for numbering element groups, as set forth in the Handbook of Chemistry and Physics, $81^{st}$ Edition (CRC Press, 2000).

By "luminescence" is meant the process of emitting electromagnetic radiation (light) from an object. Luminescence results when a system undergoes a transition from an excited state to a lower energy state with a corresponding release of energy in the form of a photon. These energy states can be electronic, vibrational, rotational, or any combination thereof. The transition responsible for luminescence can be stimulated through the release of energy stored in the system chemically or added to the system from an external source. The external source of energy can be of a variety of types including chemical, thermal, electrical, magnetic, electromagnetic, and physical, or any other type of energy source capable of causing a system to be excited into a state higher in energy than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

The term "monodisperse" refers to a population of particles (e.g., a colloidal system) wherein the particles have substantially identical size and shape. For the purpose of the present invention, a "monodisperse" population of particles means that at least about 60% of the particles, preferably about 75% to about 90% of the particles, fall within a specified particle size range. A population of monodisperse particles deviates less than 10% rms (root-mean-square) in diameter and preferably less than 5% rms.

The phrase "one or more sizes of nanoparticles" is used synonymously with the phrase "one or more particle size distributions of nanoparticles." One of ordinary skill in the art will realize that particular sizes of nanoparticles such as semiconductor nanocrystals are actually obtained as particle size distributions.

By use of the term "narrow wavelength band" or "narrow spectral linewidth" with regard to the electromagnetic radiation emission of the semiconductor nanocrystal is meant a wavelength band of emissions not exceeding about 60 nm, and preferably not exceeding about 30 nm in width, more preferably not exceeding about 20 nm in width, and symmetric about the center. It should be noted that the bandwidths referred to are determined from measurement of the full width of the emissions at half peak height (FWHM), and are appropriate in the range of 200 nm to 2000 nm.

By use of the term "a broad wavelength band," with regard to the excitation of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal). This onset occurs near to, but at slightly higher energy than the "narrow wavelength band" of the emission. This is in contrast to the "narrow absorption band" of dye molecules, which occurs near the emission peak on the high energy side, but drops off rapidly away from that wavelength and is often negligible at wavelengths further than 100 nm from the emission.

The term "emission peak" refers to the wavelength of light within the characteristic emission spectra exhibited by a particular semiconductor nanocrystal size distribution that demonstrates the highest relative intensity.

The term "excitation wavelength" refers to light having a wavelength lower than the emission peak of the semiconductor nanocrystal used in the first detection reagent.

A "hydrophobic" compound (e.g., a "hydrophobic" monomer) is one that will transfer from an aqueous phase to an organic phase, specifically from water to an organic, water-immiscible nonpolar solvent with a dielectric constant $\leq 5$, with a partition coefficient of greater than about 50%. A "hydrophobic monomer unit" refers to a hydrophobic monomer as it exists within a polymer. A "hydrophobic region" refers to a hydrophobic molecular segment, e.g., a molecular segment within a polymer. A "hydrophobic region" may be a single hydrophobic monomer unit or two or more hydrophobic monomer units that may be the same or different and may or may not be adjacent.

A "hydrophilic" compound (e.g., a "hydrophilic" monomer) is one that will transfer from an organic phase to an aqueous phase, specifically from an organic, water-immiscible nonpolar solvent with a dielectric constant $\leq 5$ to water, with a partition coefficient of greater than about 50%. A "hydrophilic monomer unit" refers to a hydrophilic monomer as it exists in a polymeric segment or polymer. A "hydrophilic region" refers to a hydrophilic molecular segment, e.g., a hydrophilic molecular segment within a polymer. A "hydrophilic region" may be a single hydrophilic monomer unit or two or more hydrophilic monomer units that may be the same or different and may or may not be adjacent.

The term "ionizable" refers to a group that is electronically neutral at a specific pH, but can be ionized and thus rendered positively or negatively charged at higher or lower pH, respectively.

The term "alkyl" as used herein refers to a branched or unbranched saturated hydrocarbon group of 1 to approximately 24 carbon atoms, such as methyl, ethyl, n-propyl, isopropyl, n-butyl, isobutyl, t-butyl, octyl, decyl, tetradecyl, hexadecyl, eicosyl and tetracosyl, as well as cycloalkyl groups such as cyclopentyl and cyclohexyl. The term "lower alkyl" intends an alkyl group of 1 to 4 carbon atoms, and thus includes methyl, ethyl, n-propyl, isopropyl, n-butyl, isobutyl and t-butyl.

The term "alkylene" as used herein refers to a difunctional saturated branched or unbranched hydrocarbon chain containing from 1 to approximately 24 carbon atoms, typically 1 to approximately 12 carbon atoms, and includes, for example, methylene ($-CH_2-$), ethylene ($-CH_2-CH_2-$), propylene ($-CH_2-CH_2-CH_2-$), 2-methylpropylene ($-CH_2-CH(CH_3)-CH_2-$), hexylene ($-(CH_2)_6-$), and the like. "Lower alkylene," as in the lower alkylene linkage of the optional coupling agent herein, refers to an alkylene group of 1 to 4 carbon atoms.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although not necessarily, alkenyl groups herein contain 2 to about 12 carbon atoms. The term "lower alkenyl" intends an alkenyl group of 2 to 4 carbon atoms, and the term "alkenylene" refers to a difunctional alkenyl group, in the same way that the term "alkylene" refers to a difunctional alkyl group.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of 2 to 4 carbon atoms, preferably 3 or 4 carbon atoms.

The term "heteroatom-containing" and the prefix "hetero-," as in "heteroatom-containing alkyl" and "heteroalkyl," refer to a molecule or molecular fragment in which one or more carbon atoms is replaced with an atom other carbon, e.g., nitrogen, oxygen, sulfur, phosphorus or silicon.

The term "alkoxy" as used herein refers to a substituent $-O-R$ wherein R is alkyl as defined above. The term "lower alkoxy" refers to such a group wherein R is lower alkyl as defined above, e.g., methoxy, ethoxy and the like.

The term "aryl" as used herein, and unless otherwise specified, refers to an aromatic moiety containing 1 to 3 aromatic rings. For aryl groups containing more than one aromatic ring, the rings may be fused or linked. Aryl groups are optionally substituted with one or more inert, nonhydrogen substituents per ring; suitable "inert, nonhydrogen" substituents include, for example, halo, haloalkyl (preferably halo-substituted lower alkyl), alkyl (preferably lower alkyl), alkenyl (preferably lower alkenyl), alkynyl (preferably lower alkynyl), alkoxy (preferably lower alkoxy), alkoxycarbonyl (preferably lower alkoxycarbonyl), carboxy, nitro, cyano and sulfonyl. Unless otherwise indicated, the term "aryl" is also intended to include heteroaromatic moieties, i.e., aromatic heterocycles. Generally, although not necessarily, the heteroatoms will be nitrogen, oxygen or sulfur. The term "arylene" refers to a difunctional aryl moiety in the same way that the term "alkylene" refers to a difunctional alkyl group.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The term "haloalkyl" refers to an alkyl group in which at least one of the hydrogen atoms in the group has been replaced with a halogen atom.

The term "peptide" refers to oligomers or polymers of any length wherein the constituent monomers are alpha amino acids linked through amide bonds, and encompasses amino acid dimers as well as polypeptides, peptide fragments, peptide analogs, naturally occurring proteins, mutated, variant or chemically modified proteins, fusion proteins, and the like. The amino acids of the peptide molecules may be any of the twenty conventional amino acids, stereoisomers (e.g., D-amino acids) of the conventional amino acids, structural variants of the conventional amino acids, e.g., iso-valine, or non-naturally occurring amino acids such as α,α-disubstituted amino acids, N-alkyl amino acids, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine. In addition, the term "peptide" encompasses peptides with posttranslational modifications such as glycosylations, acetylations, phosphorylations, and the like. The term "oligonucleotide" is used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the oligonucleotide. More particularly, the term includes polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers, providing that the polymers contain nucleobases in a configuration that allows for base pairing and base stacking, such as is found in DNA and RNA. There is no intended distinction in length between the terms "polynucleotide," "oligonucleotide," "nucleic acid" and "nucleic acid molecule," and these terms refer only to the primary structure of the molecule. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

The term "polymer" is used herein in its conventional sense to refer to a compound having two or more monomer units, and is intended to include linear and branched polymers, the term "branched polymers" encompassing simple branched structures as well as hyperbranched and dendritic polymers. The term "monomer" is used herein to refer to compounds that are not polymeric. "Polymers" herein may be naturally occurring, chemically modified, or chemically synthesized.

The term "water-dispersible" as used herein refers to an essentially unaggregated dispersion of particles, such that discrete particles of approximately 2 nm to 50 nm can be sustained indefinitely at high concentrations (10–20 $\mu$M).

The term "binding pair" refers to first and second molecules that specifically bind to each other. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. The terms "affinity molecule" and "target analyte" are also used herein to refer to the first and second members of a binding pair, respectively. Exemplary binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor—receptor agonist or antagonist (e.g., acetylcholine receptor-acetylcholine or an analog thereof), IgG-protein A, lectin-carbohydrate, enzyme—enzyme cofactor, enzyme—enzyme inhibitor, and complementary polynucleotide pairs capable of forming nucleic acid duplexes), and the like.

A "nanoparticle conjugate" refers to a nanoparticle linked, through an outer layer of an amphipathic dispersant, to a member of a "binding pair" that will selectively bind to a detectable substance present in a sample, e.g., a biological sample. The first member of the binding pair linked to the nanoparticle can comprise any molecule, or portion of any molecule, that is capable of being linked to the nanoparticle and that, when so linked, is capable of specifically recognizing the second member of the binding pair.

All molecular weights specified herein are number average molecular weights.

II. The Nanoparticles:

Prior to surface modification with a multiply amphipathic dispersant, the nanoparticles of the invention are nanoparticles with hydrophobic surfaces, the particles having a diameter in the range of about 1 nm to about 1000 nm, preferably in the range of about 2 nm to about 50 nm, more preferably in the range of about 2 nm to about 20 nm. Generally, the nanoparticles will be comprised of a semiconductive or metallic material, with semiconductive nanoparticles preferred. Also, as will be explained in greater detail below, the semiconductive or metallic material typically has a coating of a hydrophobic passivating layer resulting from the use of solvents and/or surfactants during nanoparticle manufacture. The hydrophobic surfaces of the nanoparticles have affinity for and thus serve to attach the amphipathic dispersant by virtue of the hydrophobic regions within the dispersant.

Semiconductive nanoparticles may be composed of an organic semiconductor material or an inorganic semiconductor material. Organic semiconductor materials will generally be conjugated polymers. Suitable conjugated polymers include, for example, cis and trans polyacetylenes, polydiacetylenes, polyparaphenylenes, polypyrroles, polythiophenes, polybithiophenes, polyisothianaphthene, polythienylvinylenes, polyphenylenesulfide, polyaniline, polyphenylenevinylenes, and polyphenylenevinylene derivatives, e.g., poly(2-methoxy-5-(2-ethylhexyloxy)-1,4-phenylene vinylene ("MEH-PPV") (see U.S. Pat. No. 5,189,136 to Wudl et al.), poly (2,5-bischelostanoxy-1,4-phenylene vinylene) ("BCHA-PPV") (e.g., as described in International Patent Publication No. WO 98/27136), and poly(2-N,N-dimethylamino phenylene vinylene)(described in U.S. Pat. No. 5,604,292 to Stenger-Smith et al.). Inorganic semiconductive nanoparticles are, however, preferred, and are optimally crystalline in nature; such nanoparticles are termed "semiconductor nanocrystals" herein. Semiconductor nanocrystals are capable of luminescence, generally fluorescence, when excited by light. Currently, detection of biological compounds by photoluminescence utilizes fluorescent organic dyes and chemiluminescent compounds. The use of semiconductor nanocrystals as luminescent markers, particularly in biological systems, provides advantages over existing fluorescent dyes. Many of these advantages relate to the spectral properties of nanocrystals, e.g., the ability to control the composition and size of nanocrystals enables one to construct nanocrystals with fluorescent emissions at any wavelength in the UV-visible-IR regions. With respect to composition, for example, semiconductor nanocrystals that emit energy in the visible range include, but are not limited to, CdS, CdSe, CdTe, ZnSe, ZnTe, GaP, and GaAs. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN. For any particular nanocrystal composition, it is also possible to tune the emission to a desired wavelength by controlling particle size distribution. In preferred embodiments, 5–20 discrete emissions (five to twenty different size populations or distributions distinguishable from one another), more preferably 10–15 discrete emissions, are obtained for any particular composition, although one of ordinary skill in the art will realize that fewer than five emissions and more than twenty emissions could be obtained depending on the monodispersity of the semiconductor nanocrystal particle population. If high information density is required, and thus a greater number of distinct emissions, the nanocrystals are preferably substantially monodisperse within the size range given above.

As explained above, "monodisperse" refers to a population of particles (e.g., a colloidal system) in which the particles have substantially identical size and shape. In preferred embodiments for high information density applications, monodisperse particles deviate less than 10% rms in diameter, and preferably less than 5% rms. Monodisperse semiconductor nanocrystals have been described in detail in Murray et al. (1993) *J. Am. Chem. Soc.* 115:8706, and in Murray, "Synthesis and Characterization of II–VI Quantum Dots and Their Assembly into 3-D Quantum Dot Superlattices," doctoral dissertation, Massachusetts Institute of Technology (1995). One of ordinary skill in the art will also realize that the number of discrete emissions that can be distinctly observed for a given composition depends not only upon the monodispersity of the particles, but also on the deconvolution techniques employed. Semiconductor nanocrystals, unlike dye molecules, can be easily modeled as Gaussians and therefore are more easily and more accurately deconvoluted.

However, for some applications, high information density will not be required and it may be more economically attractive to use more polydisperse particles. Thus, for applications that do not require high information density, the linewidth of the emission may be in the range of 40–60 nm.

Semiconductor nanocrystals may be made using techniques known in the art. See, e.g., U.S. Pat. Nos. 6,048,616, 5,990,479, 5,690,807, 5,505,928 and 5,262,357, as well as International Patent Publication No. WO 99/26299, published May 27, 1999. In particular, exemplary materials for use as semiconductor nanocrystals in the biological and chemical assays of the present invention include, but are not limited to, those described above, including Group 2-16, 12-16, 13-15 and 14 semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof.

In a preferred embodiment, the surface of the semiconductor nanocrystal is modified to enhance the efficiency of the emissions, prior to surface modification with the multiply amphipathic dispersant, by adding an overcoating layer or shell to the semiconductor nanocrystal. The shell is preferred because at the surface of the semiconductor nanocrystal, surface defects can result in traps for electrons or holes that degrade the electrical and optical properties of the semiconductor nanocrystal. An insulating layer at the surface of the semiconductor nanocrystal provides an atomically abrupt jump in the chemical potential at the interface that eliminates energy states that can serve as traps for the electrons and holes. This results in higher efficiency in the luminescent process.

Suitable materials for the shell include semiconductor materials having a higher bandgap energy than the semiconductor nanocrystal core. In addition to having a bandgap energy greater than the semiconductor nanocrystal core, suitable materials for the shell should have good conduction and valence band offset with respect to the core semiconductor nanocrystal. Thus, the conduction band is desirably higher and the valence band is desirably lower than those of the core semiconductor nanocrystal. For semiconductor nanocrystal cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet regions may be used. Exemplary materials include ZnS, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. The preparation of a coated semiconductor nanocrystal may be found in, e.g., Dabbousi et al. (1997) *J. Phys. Chem. B* 101:9463, Hines et al. (1996) *J. Phys. Chem.* 100: 468–471, Peng et al. (1997) *J. Am. Chem. Soc.* 119:7019–7029, and Kuno et al. (1997) *J. Phys. Chem.* 106:9869.

The nanoparticles of the invention may also be metallic. Such particles are useful, for example, in surface enhanced Raman scattering (SERS), which employs nanometer-size particles onto which Raman active moieties (e.g., a dye or pigment, or a functional group exhibiting a characteristic Raman spectrum) are adsorbed or attached. Metallic nanoparticles may be comprised of any metal or metallic alloy or composite, although for use in SERS, a SERS active metal is used, e.g., silver, gold, copper, lithium, aluminum, platinum, palladium, or the like. In addition, the particles can be in a core-shell configuration, e.g., a gold core may be encased in a silver shell; see, e.g., Freeman et al. (1996) *J. Phys. Chem.* 100:718–724, or the particles may form small aggregates in solution. Kneipp et al. (1998) *Applied Spectroscopy* 52:1493.

Generally, and as alluded to above, the unmodified nanoparticles—and thus the inner core of the present surface-modified nanoparticles—also comprise a hydrophobic coating on the semiconductive or metallic material resulting from solvents and/or surfactants used in nanoparticle manufacture. For example, semiconductive nanoparticles, as manufactured, will typically have a water-insoluble organic coating that has affinity for the semiconductive material, the coating comprised of a passivating layer resulting from use of a coordinating solvent such as hexyldecylamine or a trialkyl phosphine or trialkyl phosphine oxide, e.g., trioctylphosphine oxide (TOPO), trioctylphosphine (TOP), or tributylphosphine (TBP). Hydrophobic surfactants typically used in the manufacture of metallic nanoparticles and forming a coating thereon include, by way of example, octanethiol, dodecanethiol, dodecylamine, and tetraoctylammonium bromide. Metallic inner cores will typically have a surfactant coating that has affinity for the metallic material, the coating similarly deriving from surfactant compounds used in the manufacture of metallic nanoparticles. The surfactant coating is comprised of a hydrophobic surfactant.

III. The Dispersant:

The dispersant used to modify the hydrophobic surface of the nanoparticles is a multiply amphipathic dispersant, i.e., a compound having two or more hydrophobic regions and two or more hydrophilic regions. In a preferred embodiment, the multiply amphipathic dispersant is polymeric, and may be composed of either a linear or branched polymer, whether naturally occurring, chemically modified, or chemically synthesized. Structurally, polymers are classified as either linear or branched wherein the term "branched" generally means that the individual molecular units (i.e., monomer units) of the branches are discrete from the polymer backbone, and may or may not have the same chemical constitution as the polymer backbone.

As will be appreciated by those of ordinary skill in the art, the simplest branched polymers are the "comb branched" polymers wherein a linear backbone bears one or more essentially linear pendant side chains. This simple form of branching may be regular or irregular (in the latter case, the branches are distributed in non-uniform or random fashion on the polymer backbone). An example of regular comb branching is a comb branched polystyrene as described by Altores et al. (1965) *J. Polymer Sci., Part A* 3:4131–4151, and an example of irregular comb branching is illustrated by the graft copolymers described by Sorenson et al. in *Preparative Methods of Polymer Chemistry*, 2nd Ed., Interscience Publishers, pp. 213–214 (1968).

The amphipathic dispersant may also be a branched polymer in the form of a cross-linked or network polymer, i.e., a polymeric structure wherein individual polymer chains or branches are connected through the use of bifunctional compounds; e.g., acrylic acid monomer units bridged or crosslinked with a diamine linker. In this type of branching, many of the individual branches are not linear in that each branch may itself contain side chains pendant from a linear chain and it is not possible to differentiate between the backbone and the branches. More importantly, in network branching, each polymer macromolecule (backbone) is cross-linked at two or more sites to other polymer macromolecules. Also, the chemical constitution of the cross-linkages may vary from that of the polymer macromolecules. In this cross-linked or network branched polymer, the various branches or cross-linkages may be structurally similar (termed "regularly" cross-linked) or they may be structurally dissimilar (termed "irregularly" cross-linked).

The amphipathic dispersant may also have other structural configurations, e.g., it may be a star/comb-branched type polymer, as described in U.S. Pat. Nos. 4,599,400 and 4,690,985, or a rod-shaped dendrimer as disclosed in U.S. Pat. No. 4,694,064.

Particularly preferred amphipathic dispersants herein are hyperbranched (containing two or more generations of branching) or dendrimeric. In contrast to hyperbranched polymers, dendrimers are regularly branched macromolecules with a branch point at each repeat unit. Also, hyperbranched polymers are obtained via a polymerization reaction, while most regular dendrimers are obtained by a series of stepwise coupling and activation steps. Examples of dendrimers include the polyamidoamine (PAMAM) Starburst® dendrimers of Tomalia et al. (1985) *Polym. J.* 17:117, the convergent dendrimers of Hawker et al. (1990) *J. Am. Chem. Soc.* 112:7638, and diaminobutane dendrimers, described in Tomalia et al. (1990) *Angew. Chem., Int. Ed. Engl.* 29:135–175. With both hyperbranched polymers and dendrimers, however, the increased number of hydrophobic and hydrophilic regions amplifies the effect of the dispersant on the nanoparticle core, with respect to both affinity for the nanoparticle surface (i.e., affinity of the hydrophobic regions of the dispersant for the hydrophobic surface of the nanoparticle) and water dispersibility (as a result of the increased number of hydrophilic regions or segments).

The hydrophilic regions represent approximately 30 wt. % to 75 wt. % of the amphipathic dispersant, and are comprised of at least one monomer unit containing an ionizable or polar moiety, preferably an ionizable moiety such as a carboxylic acid, sulfonic acid, phosphonic acid or amine substituent. Examples of hydrophilic monomer units include, but are not limited to:

water-soluble ethylenically unsaturated $C_3$–$C_6$ carboxylic acids, such as acrylic acid, alkyl acrylic acids (particularly methacrylic acid), itaconic acid, maleic acid, fumaric acid, acrylamidomethyl-propanesulfonic acid, vinyl sulfonic acid, vinyl phosphonic acid, vinyl-lactic acid, and styrene sulfonic acid;

allylamine and allylamine salts formed with an inorganic acid, e.g., hydrochloric acid;

di-$C_1$–$C_3$-alkylamino-$C_2$–$C_6$-alkyl acrylates and methacrylates such dimethylaminoethyl acrylate, dimethylaminoethyl methacrylate, diethylaminoethyl acrylate, diethylaminoethyl methacrylate, dimethylaminopropyl acrylate, dimethylaminobutyl acrylate, dimethylaminoneopentyl acrylate and dimethylaminoneopentyl methacrylate;

olefinically unsaturated nitriles, such as acrylonitrile;

diolefinically unsaturated monomers, particularly diallylammonium compounds such as dimethyldiallylammonium chloride, dimethyldiallylammonium bromide, diethyldiallylammonium chloride, methyl-t-butyldiallylammonium methosulfate, methyl-n-propyldiallylammonium chloride, dimethyldiallylammonium hydrogensulfate, dimethyldiallylammonium dihydrogenphosphate, di-n-butyldiallylammonium bromide, diallylpiperidinium bromide, diallylpyrrolidinium chloride and diallylmorpholinium bromide;

N-vinylpyrrolidone;

N-vinylformamide;

acrylamide and substituted acrylamides, such as N-methylolacrylamide and $C_1$–$C_3$ alkyl acrylamides, particularly methacrylamide;

N-vinylimidazole and N-vinylimidazoline; and other monomers, typically ethylenically unsaturated monomers, preferably vinyl monomers, substituted with at least one hydrophilic functionality such as a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, a nitrate, an amine, an ammonium, or an alkyl ammonium group —[NHRR$^2$R$^2$]$^+$, wherein R$^1$ and R$^2$ are alkyl substituents and the group is associated with a negatively charged anion, e.g., a halogen ion, nitrate, etc. The hydrophilic functionality may be directly bound to a carbon atom in the polymer backbone, but will usually be bound through a linkage that provides some degree of spacing between the polymer backbone and the hydrophilic functional group. Suitable linkages include, but are not limited to, branched or unbranched alkylene, branched or unbranched alkenylene, branched or unbranched heteroalkylene (typically alkylene containing one or more ether or —NH— linkages) a branched or unbranched heteroalkenylene (again, typically alkenylene containing one or more ether or —NH— linkages), arylene, heteroarylene, alkarylene, aralkylene, and the like. The linkage will typically contain 2 to 24, more typically 2 to 12, carbon atoms.

The hydrophilic regions may also be composed of partially or fully hydrolyzed poly(vinyl alcohol), poly(ethylene glycol), poly(ethylene oxide), highly hydrated poly(alkylene oxides) such as poly(ethylene oxide), cellulosic segments (e.g., comprised of cellulose per se or cellulose derivatives such as hydroxypropyl cellulose, hydroxyethyl cellulose, hydroxypropyl methyl cellulose, methyl cellulose, ethyl cellulose, cellulose acetate, and the like), and polysaccharides such as chitosan or dextran.

The hydrophobic regions represent approximately 25 wt. % to 90 wt. % of the amphipathic dispersant, and are comprised of at least one non-ionizable, nonpolar monomer unit, facilitating noncovalent association with the hydrophobic surface of the nanoparticle. Examples of such monomer units include, but are not limited to:

acrylates such as methacrylate, methyl methacrylate, ethyl methacrylate, butyl methacrylate, isobutyl methacrylate, hexyl methacrylate, isodecyl methacrylate, lauryl methacrylate, phenyl methacrylate, isopropyl acrylate, isobutyl acrylate and octadecylacrylate, alkylenes such as ethylene and propylene;

$C_4$–$C_{12}$-alkyl-substituted ethyleneimine;

alkyl acrylamides wherein the alkyl group is larger than lower alkyl (particularly alkyl acrylamides wherein the alkyl group has six or more carbon atoms, typically six to twelve carbon atoms, such as hexylacrylamide, octylacrylamide, and the like);

styrene and hydrophobically derivatized styrenes (i.e., styrene substituted with one or more hydrophobic substituents, e.g., $C_5$–$C_{12}$ hydrocarbyl groups);

vinyl ether;

vinyl esters such as vinyl acetate; and vinyl halides such as vinyl chloride.

The hydrophobic regions may also be composed of polychloroprene, polybutadiene, polysiloxane, polydimethylsiloxane, polyisobutylene or polyurethane blocks, or they may be polycondensates of 2-poly (hydroxyalkanoic acids) such as 2-hydroxypropanoic acid, 2-hydroxybutanoic acid, 2-hydroxyisobutanoic acid, 2-hydroxyheptanoic acid, 10-hydroxydecanoic acid, 12-hydroxydodecanoic acid, 12-hydroxystearic acid, 16-hydroxyhexadecanoic acid, 2-hydroxystearic acid, 2-hydroxyvaleric acid or the corresponding condensates obtained from lactones, condensates of diols and dicarboxylic acids such as polyethylene adipate, or polylactams such as polycaprolactam.

Any of the aforementioned monomer units and polymer segments can be modified using techniques and reagents routinely used by those of ordinary skill in the art. Such modifications include, for example, routine substitutions, additions of chemical groups such as alkyl groups and alkylene groups, hydroxylations, oxidations, and the like. Such branched polymers, composed of hydrophobic segments and hydrophilic segments, are typically comprised of (1) a hydrophobic backbone with hydrophilic branches, (2) a hydrophilic backbone with hydrophobic branches, or (3) a backbone that may be either hydrophobic or hydrophilic, and is substituted with both hydrophilic and hydrophobic branches. Such polymers can be prepared by any suitable method readily known to those of ordinary skill in the art and/or described in the pertinent texts and literature. Polymers of type (1), for example, can be prepared by copolymerization of a hydrophobic monomer with a second monomer that includes suitable reactive groups through which the hydrophilic side chains (branches) can be grafted to the backbone. Alternatively, type (1) polymers can be prepared by polymerizing a single hydrophobic monomer with a suitable reactive side group, and a fraction of those reactive side groups can be modified post-polymerization by grafting hydrophilic side chains. Analogously, polymers of type (2) can be prepared by copolymerization of a hydrophilic monomer with a second monomer that includes suitable reactive groups through which the hydrophobic side chains (branches) can be grafted to the backbone. Alternatively, type (2) polymers can be prepared by polymerizing a single hydrophilic monomer with a suitable reactive side group, and a fraction of those reactive side groups can be modified post-polymerization by grafting hydrophobic side chains. Type (3) polymers can be prepared by first synthesizing a linear polymer having reactive sites throughout the backbone, and then grafting hydrophilic and hydrophobic side chains onto the backbone in a fashion that may or may not be ordered.

Particularly preferred amphipathic dispersants include acrylic acid and methacrylic acid polymers modified to include hydrophobic regions, as well as copolymers of acrylic acid and/or methacrylic acid with hydrophobic comonomers such as alkyl acrylamides. Examples of such polymers are poly(acrylic acid-co-octylacrylamide), poly (acrylic acid-co-hexylacrylamide), poly(methacrylic acid-co-octylacrylamide), and poly(methacrylic acid-co-hexylacrylamide), with poly(acrylic acid-co-octylacrylamide) most preferred. The specific methodology used to synthesize polymers suitable as the multiply amphipathic dispersant will depend on the particular monomer types that are employed. As will be appreciated by those of ordinary skill in the art, suitable polymerization techniques include step polymerization, radical chain polymerization, emulsion polymerization, ionic chain polymerization, chain copolymerization, ring-opening polymerization, living polymerization, polycondensation reactions, and graft polymerization. In a preferred embodiment, the amphipathic dispersant is formed by addition polymerization of ethylenically unsaturated monomers. Such polymerization reactions are generally catalyzed using metallic catalysts (e.g., transition metal-based metallocenes, Ziegler-Natta catalysts, Brookhart-type catalysts, etc.) and typically involve contacting the monomer(s), catalyst and a catalyst activator (e.g., methyl aluminoxane, or "MAO") at a suitable temperature at reduced, elevated or atmospheric pressure, under an inert atmosphere, for a time effective to produce the desired polymer. An added solvent may, if desired, be employed, or the monomeric compounds may serve as solvent. The reaction may be conducted under solution or slurry conditions, in a suspension, or in the gas phase. As alluded to above, branched polymers can be prepared using this technique by introducing reactive sites into the polymer backbone during polymerization (e.g., by incorporating some fraction of monomer units having a pendant reactive site), followed by synthesis or grafting of branches at the reactive sites.

In a preferred embodiment, the amphipathic dispersant is comprised of a hydrophilic backbone that has been modified to contain hydrophobic anchoring groups, i.e., hydrophobic side chains that serve to "anchor" the dispersant to the nanoparticle surface. For example, hydrophilic polymers containing pendant carboxylic acid groups (e.g., as in poly (acrylic acid), $[-(CH_2CH(CO_2H)]_n)$ can be readily modified to contain a controlled number of branched or unbranched hydrophobic side chains using methods known in the art. In one such method, the pendant carboxylic acid groups of poly(acrylic acid) can be activated with a suitable activating agent, e.g., thionyl chloride or a carbodiimide, followed by reaction with a long chain alkylamine, e.g., a $C_4C_{12}$ alkylamine such as octylamine, and finally with a hydrolyzing agent such as water. Depending on the relative quantities of the alkylamine and the hydrolyzing agent, the resulting polymer is an amphipathic polymer with a hydrophilic backbone (by virtue of the carboxylic acid groups present after partial hydrolysis) and hydrophobic side chains (the long chain alkyl group attached to the backbone through an amide linkage).

Within the aforementioned group of hydrophobically modified hydrophilic polymers are hydrophobically modified peptides, preferably hydrophobically modified synthetic polypeptides. The use of synthetic polypeptides allows for control over a number of factors, including the monodispersity of the molecular weight of the hydrophilic backbone, the number and position of modifiable groups on the backbone, and the regularity of the modification, i.e., whether the hydrophobic groups are randomly distributed throughout the polypeptide chain or present in an ordered, "regular" fashion.

Suitable polypeptides are triblock (A-B-A) copolymers, for example, triblock copolymers of aspartate and norleucine, in which case polynorleucine is preferably the central block "B." Such a triblock copolymer provides a region rich in hydrophobic side chains. In one alternative, the central block "B" can comprise a hydrophilic amino acid, for example, poly(lysine), which can be modified via standard chemistries to include hydrophobic side chains. The carboxylate-rich aspartate side chains (A) provide the polar, ionic groups that not only aid in rendering the nanocrystal water dispersible, but provide reactive sites or functionalizable moieties for further chemistry, such as conjugation to affinity molecules.

The polypeptide compositions of the present invention may also be monofunctional in nature, e.g., polylysine or polyaspartate, diblock copolymers (A-B) or triblock copolymers of three different amino acids (A-B-C). These compositions are also not restricted to lysine or aspartate, but may make use of any number of combinations of the known amino acids. Generally, the hydrophobic regions of a polypeptide are comprised of at least one hydrophobic amino acid and the hydrophilic regions are comprised of at least one hydrophilic amino acid. As will be appreciated by those of ordinary skill in the art, hydrophobic amino acids include, for example, alanine, glycine, valine, leucine, isoleucine, norleucine, proline, phenylalanine, methionine, tryptophane, cysteine, and includes hydrophilic amino acids modified to include hydrophobic side chains, while hydrophilic amino acids include aspartic acid, glutamic acid, lysine, arginine, histidine, asparagine, glutamine, serine, threonine and tyrosine.

The amphipathic dispersant generally although not necessarily has a molecular weight in the range of approximately 500 to 50,000, preferably in the range of approximately 1000 to 10,000, more preferably in the range of approximately 1000 to 5000. The dispersant may be modified so as to contain functionalizable sites useful for covalent or noncovalent attachment to an external molecular moiety. The functionalizable sites may be present in addition to the ionizable groups discussed above, or the ionizable groups may themselves serve as functionalizable sites suitable for binding an external molecular moiety. Functionalizable sites include, for example, any of the conventional functional groups that are modified using simple, conventional chemical techniques, e.g., amino groups, nitriles, carboxylic acids, esters, acid chlorides, and the like. Preferably, although not necessarily, the functionalizable sites are spaced apart from the dispersant structure by an inert linking moiety, e.g., an alkylene or oxyalkylene chain, typically composed of about 2 to 20 carbon atoms, preferably about 4 to 10 carbon atoms, or other linking moieties such as those described above with respect to the spacer linkages that may be present linking hydrophilic functional groups to the polymer backbone.

IV. Preparation of the Surface-modified Nanoparticles:

Hydrophobic nanoparticles may be rendered water dispersible by surface modification with the amphipathic dispersant. That is, the hydrophobic regions of the dispersant associate with the hydrophobic nanoparticle surface, and the hydrophilic regions are externally facing and provide water dispersibility. Surface modification of the nanoparticles is carried out as follows.

Initially, a solution of the amphipathic dispersant is prepared by admixing the selected amphipathic dispersant with a suitable nonaqueous solvent, preferably a nonpolar, water-immiscible solvent such as n-hexane or chloroform. Ionizable groups on the dispersant, if present, are then converted to salt form by treatment with an appropriate acid or base, which serves as an ionizing agent. For ionizable acidic groups, suitable bases are generally inorganic bases, e.g., ammonium hydroxides or hydroxides of alkali metals (e.g., sodium or potassium) or alkaline earth metals (e.g., magnesium or calcium). The hydrophobic nanoparticles are dispersed in the same solvent, either before or after the aforementioned ionization step. Typically, however, the nanoparticles are added after ionization, preferably dropwise, to a stirring solution of the ionized dispersant. Alternatively, the nanoparticles may be dispersed in the solvent at the outset, and the dispersant added thereto. As another alternative, two separate solutions may be prepared and mixed, with one solution containing the dispersant and the other solution containing the nanoparticles, with both solutions preferably containing the same solvent. In all cases, after preparation of the nanoparticle-dispersant-solvent admixture, the admixture is preferably stirred for several minutes to ensure complete mixing of the components.

In the next step of the process, the admixture of nanoparticles, dispersant and solvent is subjected to conditions effective to result in absorption of the dispersant by the nanoparticles. For example, the admixture may be heated or placed under vacuum to remove the solvent, such a drying process resulting in dispersant-coated nanoparticles. Alternatively, the conditions may involve changing the polarity of the solvent and/or changing the ionic state of the polymer.

Next, the dispersant-coated nanoparticles are transferred to an aqueous medium such as water, using solvent exchange (if the dispersant-coated nanoparticles are not previously dried) or addition of water or an aqueous buffer (if the dispersant-coated nanoparticles are previously dried). The aqueous buffer, if one is used, should be effective to facilitate dispersion of the nanoparticles in the aqueous medium. The water dispersion is then filtered to remove any large micellar structures formed by excess dispersant in solution that is not associated with the particles. These materials may then be used in any applications requiring aqueous-based sols of nanocrystals. Prior to using these particles one may further increase the stability of the amphipathic coating by chemically crosslinking the individual polymer chains of the dispersant coating such that each polymer has a potential multiplicity of chemical bonds to other polymer chains on the particle. One of ordinary skill in the art would recognize that the crosslinker used may be tailored to match the properties of the dispersant coating. For example, a diamine could be used to crosslink a dispersant coating containing carboxylic acids. Of particular utility are crosslinkers that carry charges or other groups capable of stabilizing the dispersed colloids as described herein. A diamino carboxylate or sulfonate and a diamino polyethylene glycol crosslinkers are especially useful. A similar chemistry would apply for crosslinkers having multiple amine moieties, such as dendrimers, modified dendrimers, and the like.

The amount of amphipathic dispersant per unit mass of the "inner core" (i.e., per unit mass of the original, unmodified nanoparticle) in the resulting dispersant-coated nanoparticles is proportional to the size and surface area of the nanoparticles. Generally, the number ratio of the dispersant to the inner core will be in the range of approximately 50:1 to approximately 5000:1. The ratio will be closer to 50:1 for smaller nanoparticles, i.e., nanoparticles less than about 5 nm in diameter (e.g., green CdSe quantum dots), and will be closer to 5000:1 for larger nanoparticles, i.e., nanoparticles about 5 nm to 10 nm in diameter (e.g., red CdSe quantum dots).

V. Nanoparticle Conjugates and Associated Compositions:

The invention additionally relates to conjugates of the present surface-modified semiconductive nanoparticles and compositions comprising those conjugates in association with a target analyte.

That is, the surface-modified semiconductive nanoparticles of the invention may be conjugated to an affinity molecule that serves as the first member of a binding pair. Generally, although not necessarily, it is the amphipathic dispersant on the nanoparticle surface that provides the means for linkage to the affinity molecule. As noted previously, ionizable groups present within the hydrophilic regions of the amphipathic dispersant may provide the means for linkage to the affinity molecule, and/or other functional groups present within or introduced into the dispersant molecule may provide the means for linkage to the affinity molecule. The linkage will generally be covalent, and suitable linkers are discussed in Section III, above. Suitable methods of conjugating molecules and molecular segments to affinity molecules are described, for example, in Hermanson, Bioconjugate Techniques (Academic Press, NY, 1996).

Such semiconductive nanoparticle "conjugates," by virtue of the affinity molecule, can be used to detect the presence and/or quantity of biological and chemical compounds, interactions in biological systems, biological processes, alterations in biological processes, or alterations in the structure of biological compounds. That is, the affinity molecule, when linked to the semiconductive nanoparticle, can interact with a biological target that serves as the second member of the binding pair, in order to detect biological processes or reactions, or to alter biological molecules or processes. Preferably, the interaction of the affinity molecule and the biological target involves specific binding, and can involve covalent, noncovalent, hydrophobic, hydrophilic, electrostatic, van der Waal's, or magnetic interaction. Preferably, the affinity molecule physically interacts with the biological target.

The affinity molecule associated with the semiconductive nanoparticles can be naturally occurring or chemically synthesized, and can be selected to have a desired physical, chemical or biological property. Such properties include, but are not limited to, covalent and noncovalent association with proteins, nucleic acids, signaling molecules, prokaryotic or eukaryotic cells, viruses, subcellular organelles and any other biological compounds. Other properties of such molecules include, but are not limited to, the ability to affect a biological process (e.g. cell cycle, blood coagulation, cell death, transcription, translation, signal transduction, DNA damage or cleavage, production of radicals, scavenging radicals, etc.), and the ability to alter the structure of a biological compound (e.g. crosslinking, proteolytic cleavage, radical damage, etc.

In a preferred embodiment, the nanoparticle conjugate is comprised of a semiconductive nanoparticle that emits light at a tunable wavelength and is associated with a nucleic acid. The association can be direct or indirect. The nucleic acid can be any ribonucleic acid, deoxyribonucleic acid, dideoxyribonucleic acid, or any derivatives and combinations thereof. The nucleic acid can also be oligonucleotides of any length. The oligonucleotides can be single-stranded, double-stranded, triple-stranded or higher order configurations (e.g. Holliday junctions, circular single-stranded DNA, circular double-stranded DNA, DNA cubes, (see Seeman (1998) *Ann. Rev. Biophys. Biomol. Struct.* 27:225248). Among the preferred uses of the present compositions and methods are detecting and/or quantitating nucleic acids as follows: (a) viral nucleic acids; (b) bacterial nucleic acids; and (c) numerous human sequences of interest, e.g. single nucleotide polymorphisms. Without limiting the scope of the present invention, nanoparticle conjugates can comprise nanocrystals associated with individual nucleotides, deoxynucleotides, dideoxynucleotides or any derivatives and combinations thereof and used in DNA polymerization reactions such as DNA sequencing, reverse transcription of RNA into DNA, and polymerase chain reactions (PCR). Nucleotides also include monophosphate, diphosphate and triphosphates and cyclic derivatives such as cyclic adenine monophosphate (cAMP). Other uses of nanoparticles conjugated to nucleic acids included fluorescence in situ hybridization (FISH). In this preferred embodiment, nanocrystals are conjugated to oligonucleotides designed to hybridize to a specific sequence in vivo. Upon hybridization, the fluorescent nanocrystal tags are used to visualize the location of the desired DNA sequence in a cell. For example, the cellular location of a gene whose DNA sequence is partially or completely known can be determined using FISH. Any DNA or RNA whose sequence is partially or completely known can be visually targeted using FISH. For example without limiting the scope of the present invention, messenger RNA (mRNA), DNA telomeres, other highly repeated DNA sequences, and other non-coding DNA sequencing can be targeted by FISH.

The nanoparticle conjugate may also comprise a surface-modified semiconductive nanoparticle as provided herein in association with a molecule or reagent for detection of biological compounds such as enzymes, enzyme substrates, enzyme inhibitors, cellular organelles, lipids, phospholipids, fatty acids, sterols, cell membranes, molecules involved in signal transduction, receptors and ion channels. The conjugate also can be used to detect cell morphology and fluid flow; cell viability, proliferation and function; endocytosis and exocytosis (Betz et al. (1996) Curr. Opin. Neurobiol. 6(3):365–71); and reactive oxygen species (e.g., superoxide, nitric oxide, hydroxyl radicals, oxygen radicals). In addition, the conjugate can be used to detect hydrophobic or hydrophilic regions of biological systems.

Conjugates of semiconductive nanocrystals also find utility in numerous other biological and non-biological applications where luminescent markers, particularly fluorescent markers, are typically used. See, for example, Haugland, R. P. Handbook of Fluorescent Probes and Research Chemicals (Molecular Probes, Eugene, Oreg. Sixth Ed. 1996; Website, www.probes.com.). Examples of areas in which the luminescent nanoparticle conjugates of the invention are useful include, without limitation, fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems. For further discussion concerning the utility of nanocrystal conjugates in the aforementioned areas, see International Patent Publication No. WO 00/17642 to Bawendi et al.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

The following examples are intended to provide those of ordinary skill in the art with a complete disclosure and description of how to make and use the novel compositions of the invention. Efforts have been made to ensure accuracy with respect to numbers used (e.g., amounts, temperatures, etc), but some experimental error and deviation should, of course, be allowed for. Unless indicated otherwise, parts are parts by weight, temperatures are in degrees centigrade, and pressure is at or near atmospheric.

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Haines & S J. Higgins, eds., 1984); *Methods in Enzymology* (Academic Press, Inc.); Kirk-Othmer's *Encyclopedia of Chemical Technology;* and House's Modern Synthetic Reactions. All patents, patent applications, patent publications, journal articles and other references cited herein are incorporated by reference in their entireties.

EXAMPLE 1

Synthesis of Hydrophobically Modified Hydrophilic Polymers:

A modified polyacrylic acid was prepared by diluting 100 g [0.48 mol COONa] of poly(acrylic acid, sodium salt) (obtained from Aldrich, molecular weight 1200) was diluted two-fold in water and acidified in a 1.0 L round bottom flask with 150 ml (1.9 mol) of concentrated HCl. The acidified polymer solution was concentrated to dryness on a rotary evaporator (100 mbar, 80° C.). The dry polymer was evacuated for 12 hours at <10 mbar to ensure water removal. A stirbar and 47.0 g (0.24 mol) of 1-[3-(dimethyl-amino)-propyl]-ethylcarbodiimide hydrochloride (EDC-Aldrich 98%) were added to the flask, then the flask was sealed and purged with $N_2$, and fit with a balloon. 500 ml of anhydrous N—N,dimethylformamide (Aldrich) was transferred under positive pressure through a cannula to this mixture; and the flask was swirled gently to dissolve the solids. 32 ml (0.19 mol) of octylamine was transferred dropwise under positive pressure through a cannula from a sealed oven-dried graduated cylinder into the stirring polymer/EDC solution, and the stirring continued for 12 hours. This solution was concentrated to <100 ml on a rotary evaporator (30 mbar, 80° C.), and the polymer was precipitated by addition of 200 ml di-$H_2O$ to the cooled concentrate, which produced a gummy white material. This material was separated from the supernatant and triturated with 100 ml di-$H_2O$ three more times. The product was dissolved into 400 ml ethyl acetate (Aldrich) with gentle heating, and basified with 200 ml di-$H_2O$ and 100 g N—N—N—N-tetramethylammonium hydroxide pentahydrate (0.55 mo) for 12 hours. The aqueous layer was removed and precipitated to a gummy white product with 400 ml of 1.27 M HCl. The product was decanted and triturated with 100 ml of di-$H_2O$ twice more, after which the aqueous washings were back-extracted into 6×100 ml portions of ethyl acetate. These ethyl acetate solutions were added to the product flask, and concentrated to dryness (100 mbar, 60° C.). The crude polymer was dissolved in 300 ml of methanol and purified in two aliquots over LH-20 (Amersham-Pharmacia-5.5 cm×60 cm column) at a 3 ml/minute flow rate. Fractions were tested by NMR for purity, and the pure fractions were pooled, while the impure fractions were re-purified on the LH-20 column. After pooling all of the pure fractions, the polymer solution was concentrated by rotary evaporation to dryness, and evacuated for 12 hours at <10 mbar. The product was a white powder (25.5 g, 45% of theoretical yield), which showed broad NMR peaks in $CD_3OD$ [δ=3.1 b (9.4), 2.3 b (9.7), 1.9 1.7 1.5 1.3 b (63.3) 0.9 bt (11.3)], and clear IR signal for both carboxylic acid (1712 $cm^{-1}$) and amide groups (1626 $cm^{-1}$, 1544 $cm^{-1}$).

EXAMPLE 2

Preparation of Surface-Modified Nanocrystals:

Twenty milliliters of 3–5 μM (3–5 nmoles) of TOPO/TOP coated CdSe/ZnS nanocrystals (see, Murray et al. (1993) *J. Am. Chem. Soc.* 115:8706) were precipitated with 20 milliliters of methanol. The flocculate was centrifuged at 3000× g for 3 minutes to form a pellet of the nanocrystals. The supernatant was thereafter removed and 20 milliliters of methanol was again added to the particles. The particles were vortexed to loosely disperse the flocculate throughout the methanol. The flocculate was centrifuged an additional time to form a pellet of the nanocrystals. This precipitation/centrifugation step was repeated an additional time. to remove any excess reactants remaining from the nanocrystal synthesis. Twenty milliliters of chloroform were added to the nanocrystal pellet to yield a freely dispersed sol.

300 milligrams of hydrophobically modified poly(acrylic acid) was dissolved in 20 ml of chloroform. Tetrabutylammonium hydroxide (1.0 M in methanol) was added to the polymer solution to raise the solution to pH 10 (pH was measured by spotting a small aliquot of the chloroform solution on pH paper, evaporating the solvent and thereafter wetting the pH paper with distilled water). Thereafter the polymer solution was added to 20 ml of chloroform in a 250 ml round bottom flask equipped with a stir bar. The solution was stirred for 1 minute to ensure complete admixture of the polymer solution. With continued stirring the washed nanocrystal dispersion described above was added dropwise to the polymer solution. The dispersion was then stirred for two minutes to ensure complete mixing of the components and thereafter the chloroform was removed in vacuo with low heat to yield a thin film of the particle-polymer complex on the wall of the flask. Twenty milliliters of distilled water were added to the flask and swirled along the walls of the flask to aid in dispersing the particles in the aqueous medium. The dispersion was then allowed to stir overnight at room temperature. At this point the nanocrystals are freely dispersed in the aqueous medium, possess pendant chemical functionalities and may therefore be linked to affinity molecules of interest using methods well known in the art for biolabeling experiments. In addition, the fact that the nanocrystals now have a highly charged surface means they can be readily utilized in polyelectrolyte layering experiments for the formation of thin films and composite materials.

EXAMPLE 3
Preparation of Nanocrystal Conjugates:

Functional and specific biological labels have been made with materials of the present invention as follows: The polymer stabilized particles from Example 1 were purified away from excess (non-absorbed) polymer and tetrabutylammonium hydroxide via tangential flow diafiltration using a 100 K polyethersulfone membrane against one liter of distilled water and one liter of 50 mM Morpholinoethanesulfonic acid buffer, pH 5.9. The purified dispersion was concentrated to 20 milliliters and 10 milliliters of this nanocrystal dispersion were activated with 79 $\mu$moles (15 mg) 1-ethyl-3-(3-dimethylaminopropyl) carbodiimide hydrochloride (EDC) and 158 $\mu$moles (34 mg) N-hydroxysulfosuccinimide for 30 minutes at room temperature. The particle dispersion was then buffer exchanged to pH 8.0 via diafiltration against 50 mM phosphate buffer, pH 8.0. When the particle dispersion reached pH 8.0, streptavidin was added to the particles at a 5:1 protein:particle ratio (175 nmoles, 10.5 mg) and the reaction mixture was incubated overnight at room temperature with stirring. After overnight incubation the conjugated particles were separated from excess, unreacted protein via tangential flow diafiltration using a 100,000 MW polyethersulfone membrane against 2 liters of phosphate buffer, 50 mM, pH 7.0.

At this point these materials can be stored in any number of biological buffers and used as fluorescent biological labels to detect biotin-labeled analytes of interest. Although streptavidin was used here as an example, the simplicity and generality of the above coupling chemistries can be efficiently extended to forming functional conjugates with any number of biological molecules of interest, such as antibodies, peptides, and oligonucleotides, for example.

EXAMPLE 4
Crosslinking of Polymer Stabilized Nanocrystals with a Dendrimer:

Ten milliliters of nanocrystals at 3.5 $\mu$M, stabilized as described in Example 2, were purified by tangential flow filtration, as described in Example 3, against 1 liter of distilled water to remove excess polymer. The nanocrystals were concentrated to 10 milliliters and the pH of the aqueous dispersion was decreased to pH 6.5 with 50 $\mu$l additions of 0.1M HCl. 67 milligrams (315 $\mu$moles) EDC were added to the stirring nanocrystal dispersion. The reaction was allowed to proceed for 10 minutes before 1 milliliter of 0.5M borate buffer (pH 8.5) containing 3.94 $\mu$moles of the crosslinking reagent Starburst® (PAMAM) Dendrimer, Generation 0, were added to the reaction mixture. The reaction mixture was stirred for 2 hours at room temperature and then transferred to a 50,000 molecular weight cut-off polyethersulfone dialysis bag. Dialysis was performed for 24 hours against 2 changes of 4 liters of water.

EXAMPLE 5
Crosslinking of Polymer Stabilized Nanocrystals with a Diamino Crosslinker:

Ten milliliters of nanocrystals at 3.5 $\mu$M, stabilized as described in Example 2, were purified by tangential flow filtration, as described in Example 3, against 1 liter of distilled water to remove excess polymer. The nanocrystals were concentrated to 10 milliliters and the pH of the aqueous dispersion was decreased to pH 6.5 with 50 $\mu$l additions of 0.1M HCl. 67 milligrams (315 $\mu$moles) EDC were added to the stirring nanocrystal dispersion. The reaction was allowed to proceed for 10 minutes before 1 milliliter of 0.5M borate buffer (pH 8.5) containing 3.94 $\mu$moles of the crosslinking reagent lysine (a diamino carboxylic acid) were added to the reaction mixture. The reaction mixture was stirred for 2 hours at room temperature and then transferred to a 50,000 molecular weight cut-off polyethersulfone dialysis bag. Dialysis was performed for 24 hours against 2 changes of 4 liters of water.

EXAMPLE 6
Preparation of Surface Modified Nanocrystals With Polypeptides:

A triblock polypeptide comprised of (Aspartate)$_4$-(Norleucine)$_8$-(Aspartate)$_4$ has been used to stabilize hydrophobic nanocrystals in water by the following method: Five milliliters of a 3.5 $\mu$M nanocrystal solution were washed as described in Example 1 and redispersed in 5 milliliters of chloroform. 75 milligrams of an (Aspartate)$_4$(Norleucine)$_8$-(Aspartate)$_4$-triblock polypeptide were dissolved in 5 milliliters of a 50:50 mixture of chloroform:methanol and the pH of the polypeptide solution was raised to 10 with aliquots of tetrabutyammonium hydroxide (1.0M in methanol). This polypeptide solution was then added to 5 milliliters of chloroform in a 50 milliliter round bottom flask. The solution was allowed to stir for 1 minute to ensure complete mixing. The washed nanocrystal dispersion in chloroform was then added dropwise to the stirring polypeptide solution and the entire mixture was allowed to stir for an additional 2 minutes before all the solvent was removed in vacuo with low heat (40 degrees Celsius) to yield a thin film of the particle-polymer complex on the wall of the flask. Five milliliters of distilled water were then added to the flask and swirled in order to aid in dispersing the nanocrystals fully in the aqueous medium. As with the nanocrystals stabilized in Example 1, these polypeptide stabilized nanocrystals can be efficiently purified away from excess polypeptide by dialysis, tangential flow filtration, or various forms of chromatography known to those skilled in the art.

We claim:

1. A water-dispersible nanoparticle comprising: an inner core comprised of a semiconductive or metallic material; a water-insoluble organic coating surrounding the inner core; and, surrounding the water-insoluble organic coating, an outer layer comprised of a multiply amphipathic dispersant molecule, wherein the dispersant molecule comprises at least two hydrophobic regions and at least two hydrophilic regions.

2. The water-dispersible nanoparticle of claim 1, wherein the inner core is comprised of a semiconductive material.

3. The water-dispersible nanoparticle of claim 2, wherein the semiconductive material is inorganic.

4. The water-dispersible nanoparticle of claim 3, wherein the semiconductive material is crystalline.

5. A composition comprising a plurality of water-dispersible nanoparticles of claim 4.

6. The water-dispersible nanoparticle of claim 2, wherein the water-insoluble organic coating is comprised of trioctylphosphine oxide, trioctylphosphine, tributylphosphine, or a mixture thereof.

7. The water-dispersible nanoparticle of claim 2, further including a shell layer between the core and the water-insoluble organic coating.

8. The water-dispersible nanoparticle of claim 7, wherein the shell layer is comprised of a semiconductive material having a band gap energy greater than that of the inner core.

9. The water-dispersible nanoparticle of claim 1, wherein the inner core is comprised of a metallic material.

10. The water-dispersible nanoparticle of claim 9, wherein the water-insoluble organic coating has a affinity for the metallic material.

11. The water-dispersible nanoparticle of claim 10, wherein the water-insoluble organic coating is comprised of a hydrophobic surfactant.

12. The water-dispersible nanoparticle of claim 11, wherein the hydrophobic surfactant is selected from the group consisting of octanethiol, dodecanethiol, dodecylamine, tetraoctylammonium bromide, and mixtures thereof.

13. The water dispersible nanoparticle of claim 1, wherein the multiply amphipathic dispersant is a polymer having two or more hydrophobic regions and two or more hydrophilic regions.

14. The water-dispersible nanoparticle of claim 13, wherein the dispersant is a linear or branched polymer.

15. The water-dispersible nanoparticle of claim 14, wherein the polymer is branched.

16. The water-dispersible nanoparticle of claim 15, wherein the polymer is hyperbranched or dendritic.

17. The water-dispersible nanoparticle of claim 13, wherein the hydrophobic regions of the polymer dispersant are each comprised of at least one non-ionizable, nonpolar monomer unit.

18. The water-dispersible nanoparticle of claim 13, wherein each of the hydrophobic regions are each comprised at least one monomer unit selected from the group consisting of ethylene, propylene, alkyl ($C_4$–$C_{12}$)-substituted ethyleneimine, an alkyl acrylate, a methacrylates, a phenyl acrylate, an alkyl acrylamides, a styrenes, a hydrophobically derivatized styrenes, a vinyl ethers, a vinyl ester, a vinyl halides, and a combinations thereof.

19. The water-dispersible nanoparticle of claim 18, wherein the hydrophobic comprised at least one monomer unit selected from an alkyl acrylate, an alkyl methacrylate, an alkyl acrylamide, and a mixture thereof.

20. The water-dispersible nanoparticle of claim 19, wherein the hydrophobic regions of the dispersant represent in the range of approximately 25 wt. % to 90 of the polymer.

21. The water-dispersible nanoparticle of claim 18, wherein the hydrophilic regions each comprised at least one monomer unit containing an ionizable or polar moiety.

22. The water-dispersible nanoparticle of claim 21, wherein the hydrophilic regions each comprised of at least one monomer unit containing an ionizable moiety.

23. The water-dispersible nanoparticle of claim 22, wherein the ionizable moiety is selected from the group consisting of carboxylic acid, sulfonic acid, phosphonic acid, and an amine substituents.

24. The water-dispersible nanoparticle of claim 13, wherein the hydrophilic regions of the dispersant each comprised at least one monomer unit containing an ionizable or polar moiety.

25. The water-dispersible nanoparticle of claim 24, wherein the hydrophilie regions each comprised at least one monomer unit containing an ionizable moiety.

26. The water-dispersible nanoparticle of claim 25, wherein the ionizable moiety is selected from the group consisting of carboxylic acid, sulfonic acid, phosphonic acid, and amine substituents.

27. The water-dispersible nanoparticle of claim 13, wherein the hydrophilic regions of the dispersant each comprised at least one monomer unit selected from the group consisting of a water-soluble ethylenically unsaturated $C_3$–$C_6$ carboxylic acids, an allylamine, an inorganic acid addition salts of an allylamines, a di-$C_1$–$C_3$-alkylamino-$C_2$–$C_6$alkyl acrylates, a methacrylates, an olefinically unsaturated nitriles, a diolefinically unsaturated monomers, N-vinyl pyrrolidone, N-vinyl formamide, an acrylamide, a lower alkyl-substituted acrylamides, a lower alkoxy-substituted acrylamides, N-vinylimidazole, N-vinylimidazoline, a styrene sulfonic acid and an alkylene oxides.

28. The water-dispersible nanoparticle of claim 27, wherein the hydrophilic regions each comprised at least one monomer unit selected from the group consisting of acrylic acid, methacrylic acid, styrene sulfonic acid, acrylamide and methacrylamide.

29. The water-dispersible nanoparticle of claim 13, wherein the hydrophilic regions of the dispersant each comprised a vinyl monomer substituted with at least one hydrophilic moiety selected from the group consisting of a carboxylate, a thiocarboxylate, an amide, an imide, a hydrazine, a sulfonate, a sulfoxide, a sulfone, a sulfite, a phosphate, a phosphonate, a phosphonium, an alcohol, a thiol, a nitrate, an amine, an ammonium, and an alkyl ammonium group-$[NHR^1R^2]^+$, wherein $R^1$ and $R^2$ are alkyl substituents.

30. The water-dispersible nanoparticle of claim 29, wherein the hydrophilic moiety is directly bound to a carbon atom in the polymer backbone of the dispersant.

31. The water-dispersible nanoparticle of claim 29, wherein the hydrophilic moiety is bound to a carbon atom in the polymer backbone of the dispersant through a linkage selected from the group consisting of alkylene, alkenylene, heteroalkylene, heteroalkenylene, arylene, heteroarylene, alkarylene, and aralkylene.

32. The water-dispersible nanoparticle of claim 13, wherein the amphipathic dispersant polymer is a copolymer of a hydrophilic monomer selected from the group consisting of acrylic acid, methacrylic acid and combinations thereof, with at least one hydrophobic alkyl ($C_6$–$C_{12}$) acrylamides monomer.

33. The water-dispersible nanoparticle of claim 32, wherein the amphipathic dispersant is poly(acrylic acid-co-octylacrylamide).

34. The water-dispersible nanoparticle of claim 33, wherein the poly(acrylic acid-co-octylacrylamide) has a molecular weight in the range of approximately 1000 to 5000.

35. The water-dispersible nanoparticle of claim 13, wherein the polymer has a molecular weight in the range of approximately 500 to 50,000.

36. The water-dispersible nanoparticle of claim 35, wherein the polymer has a molecular weight in the range of approximately 1000 to 10,000.

37. The water-dispersible nanoparticle of claim 36, wherein the polymer has a molecular weight in the range of approximately 1000 to 5000.

38. The water-dispersible nanoparticle of claim 13, wherein the polymer is a polypeptide, in which the hydrophobic regions are comprised of at least one hydrophobic amino acid and the hydrophilic regions are comprised of at least one hydrophilic amino acid.

39. The water-dispersible nanoparticle of claim 13, wherein the multiply amphipathic dispersant is crosslinked.

40. The water-dispersible nanoparticle of claim 13, wherein the polymer multiply amphiphatic dispersant contains functionalizable groups.

41. The water-dispersible nanoparticle of claim 40, wherein the functionalizable groups are bound to the multiply amphipathic dispersant through a linking moiety.

42. The water-dispersible nanoparticle of claim 1, wherein the nanoparticle is conjugated to an affinity molecule that serves as a first member of a binding pair, and the affinity molecule is selected from the group consisting of a protein, an oligonucleotide, an enzyme inhibitor, a polysaccharide, and a small molecule having a molecular weight of less than about 1500 grams/Mol.

43. The water-dispersible nanoparticle of claim 42, further comprising a second member of the binding pair associated with the first member through either covalent or noncovalent interaction.

44. The water-dispersible nanoparticle of claim 42, wherein the nanoparticle is conjugated to the affinity molecule through the multiply amphipathic dispersant.

45. A composition comprising a plurality of water-dispersible nanoparticles of claim 1.

46. The composition of claim 45, wherein the inner cores of the nanoparticles are members of a monodisperse particle population.

47. The composition of claim 46, wherein the monodisperse particle population is characterized in that when irradiated the population emits light in a bandwidth in the range of approximately 20 nm to 60 nm full width at half maximum (FWIIM).

48. The composition of claim 47, wherein the monodisperse particle population is characterized in that when irradiated the population emits light in a bandwidth in the range of approximately 20 nm to 40 nm full width at half maximum (FWIIM).

49. The composition of claim 46, wherein the monodisperse particle population is characterized in that it exhibits no more than about a 10% rms deviation in the diameter of the inner core.

50. The composition of claim 49, wherein the monodisperse particle population is characterized in that it exhibits no more than about a 5% rms deviation in the diameter of the inner core.

51. The composition of claim 46, wherein the inner core of the nanoparticles is comprised of a semiconductive material.

52. The composition of claim 51, wherein the semiconductive material is inorganic.

53. The composition of claim 52, wherein the semiconductive material is crystalline.

54. The composition of claim 53, wherein the nanoparticles further include a shell layer between the inner core and the water-insoluble organic layer.

55. The composition of claim 54, wherein the shell layer is of a semiconductive material having a band gap energy greater than that of the inner comprised core.

56. The composition of claim 46, wherein the inner core of the nanoparticles is comprised of a metallic material.

57. The composition of claim 46, wherein the multiply amphipathic dispersant is a polymer having two or more hydrophobic regions and two or more hydrophilic regions.

* * * * *

UNITED STATES PATENT AND TRADEMARK OFFICE
CERTIFICATE OF CORRECTION

PATENT NO.    : 6,649,138 B2
DATED         : November 18, 2003
INVENTOR(S)   : Edward W. Adams et al.

It is certified that error appears in the above-identified patent and that said Letters Patent is hereby corrected as shown below:

Column 15,
Line 19, delete "-$[NHRR^2R^2]^+$" and insert -- -$[NHR^1R^2]^+$ --

Column 25,
Line 36, delete "a" and insert -- an --
Line 43, delete "dodccanethiol" and insert -- dodecanethiol --
Line 61, delete "are each comprised" and insert -- comprise --
Line 65, delete "acrylamides" and insert -- acrylamide --
Lines 65 and 66, delete "styrenes" and insert -- styrene --
Line 66, delete "ethers" and insert -- ether --
Line 67, delete "halides" and insert -- halide --
Line 67, delete "combinations" and insert -- combination --

Column 26,
Line 2, delete "comprised" and insert -- regions comprise --
Line 7, after "90", insert -- wt. % --
Lines 9, 20, 23, 31, 43 and 49, delete "comprised" and insert -- comprise --
Line 12, delete "comprised of" and insert -- comprise --
Lines 17 and 28, delete "substituents" and insert -- substituent --
Line 23, delete "hydrophilie" and insert -- hydrophilic --
Line 33, delete "acids" and insert -- acid --
Line 34, delete "salts" and insert -- salt --
Line 34, delete "allylamines" and insert -- allylamine --
Line 35, delete "acrylates" and insert -- acrylate --
Line 35, delete "methacrylates" and insert -- methacrylate --
Line 36, delete "nitriles" and insert -- nitrile --
Line 37, delete "monomers" and insert -- monomer --
Lines 38 and 39, delete "acrylamides" and insert -- acrylamide --
Line 41, delete "oxides" and insert -- oxide --

UNITED STATES PATENT AND TRADEMARK OFFICE
CERTIFICATE OF CORRECTION

PATENT NO. : 6,649,138 B2
DATED : November 18, 2003
INVENTOR(S) : Edward W. Adams et al.

It is certified that error appears in the above-identified patent and that said Letters Patent is hereby corrected as shown below:

Column 27,
Lines 26 and 28, delete "13" and insert -- 1 --
Lines 13 and 17, delete "(FWIIM)" and insert -- (FWHM) --

Signed and Sealed this

Thirteenth Day of April, 2004

JON W. DUDAS
*Acting Director of the United States Patent and Trademark Office*